(12) United States Patent
Tajiri et al.

(10) Patent No.: US 10,175,189 B2
(45) Date of Patent: Jan. 8, 2019

(54) DETERMINATION DEVICE FOR DETERMINING AN IMPROVEMENT IN WATER QUALITY

(71) Applicant: TOSHIKOGYO CO., LTD., Yokohama-shi, Kanagawa (JP)

(72) Inventors: Yasuo Tajiri, Yokohama (JP); Mitsuo Ishikawa, Yokohama (JP); Nobuyuki Kamiya, Yokohama (JP)

(73) Assignee: TOSHIKOGYO CO., LTD., Yokohama-shi (JP)

( * ) Notice: Subject to any disclaimer, the term of this patent is extended or adjusted under 35 U.S.C. 154(b) by 54 days.

(21) Appl. No.: 15/313,234

(22) PCT Filed: Mar. 30, 2016

(86) PCT No.: PCT/JP2016/060352
§ 371 (c)(1),
(2) Date: Nov. 22, 2016

(87) PCT Pub. No.: WO2017/168625
PCT Pub. Date: Oct. 5, 2017

(65) Prior Publication Data
US 2018/0172614 A1 Jun. 21, 2018

(51) Int. Cl.
*G01R 27/16* (2006.01)
*G01R 27/26* (2006.01)
(Continued)

(52) U.S. Cl.
CPC ........... *G01N 27/228* (2013.01); *C02F 1/005* (2013.01); *C02F 1/30* (2013.01); *G01N 17/04* (2013.01);
(Continued)

(58) Field of Classification Search
CPC ........ G01R 27/16; G01R 27/26; G01N 27/04; G01N 27/22; G01N 33/18; G01N 33/28
See application file for complete search history.

(56) References Cited

U.S. PATENT DOCUMENTS 3,878,461 A 4/1975 Saint-Andre
4,853,638 A * 8/1989 Endou .................... G01N 27/06
324/441

(Continued)

FOREIGN PATENT DOCUMENTS

CN 102012248 A 4/2011
CN 104122376 A 10/2014
(Continued)

OTHER PUBLICATIONS

Website of Toshikogyo Co., Ltd. "Introduction of the Products.", URL http://www.biowater.co.jp/product/feature.html.
(Continued)

*Primary Examiner* — Neel Shah
(74) *Attorney, Agent, or Firm* — Oliff PLC

(57) ABSTRACT

A determination device for determining an improvement in water quality, capable of determining it in no time, is provided. The device has a first measuring device for measuring by AC terminal electric conductimetry a capacitance of a first capacitor formed between a pair of electrodes immersed in untreated water to be supplied to a water quality-improving apparatus; a second measuring device for measuring by AC terminal electric conductimetry a capacitance of a second capacitor formed between a pair of electrodes immersed in water discharged by the apparatus; and a processor for calculating a ratio (Y/X) of a capacitance Y to a capacitance X wherein the capacitance X is a capacitance of the first capacitor outputted by the first measuring device when an AC frequency is 100 Hz or less,
(Continued)

and the capacitance Y is a capacitance of the second capacitor at the same frequency outputted by the second measuring device.

9 Claims, 1 Drawing Sheet

(51) Int. Cl.
*G01N 27/04* (2006.01)
*G01N 27/22* (2006.01)
*G01N 33/18* (2006.01)
*G01N 33/28* (2006.01)
*C02F 1/00* (2006.01)
*C02F 1/30* (2006.01)
*G01N 17/04* (2006.01)
*G08B 21/18* (2006.01)
*C02F 103/02* (2006.01)

(52) U.S. Cl.
CPC ............ *G01N 27/22* (2013.01); *G01N 33/18* (2013.01); *G08B 21/182* (2013.01); *C02F 2103/02* (2013.01); *C02F 2209/05* (2013.01); *C02F 2307/14* (2013.01)

(56) References Cited

U.S. PATENT DOCUMENTS

| | | | |
|---|---|---|---|
| 5,234,601 A | | 8/1993 | Janke et al. |
| 5,435,170 A | * | 7/1995 | Voelker ................ G01N 27/221 73/53.05 |
| 5,450,358 A | | 9/1995 | Seibert et al. |
| 7,504,836 B2 | * | 3/2009 | Chambon ........... A47J 37/1266 324/698 |
| 2003/0184316 A1 | * | 10/2003 | Yamagishi ........... G01N 27/228 324/663 |
| 2011/0278168 A1 | * | 11/2011 | Zhuiykov .............. G01N 27/30 204/407 |
| 2014/0312921 A1 | | 10/2014 | Ueno et al. |
| 2014/0326340 A1 | | 11/2014 | Kuriki et al. |
| 2016/0187287 A1 | | 6/2016 | Tajiri et al. |

FOREIGN PATENT DOCUMENTS

| | | |
|---|---|---|
| JP | S63-008549 A | 1/1988 |
| JP | S64-12253 A | 1/1989 |
| JP | H5-6362 U | 1/1993 |
| JP | H07-260725 A | 10/1995 |
| JP | 2003-279524 A | 10/2003 |
| JP | 2005-321275 A | 11/2005 |
| JP | 2014-215073 A | 11/2014 |
| JP | 5780539 B1 | 9/2015 |
| WO | 2015/181859 A1 | 12/2015 |

OTHER PUBLICATIONS

May 24, 2016 International Search report issued in Patent Application No. PCT/JP2016/060352.
Jul. 25, 2018 Search Report issued in European Patent Application No. 16791289.8.

* cited by examiner

Figure 1
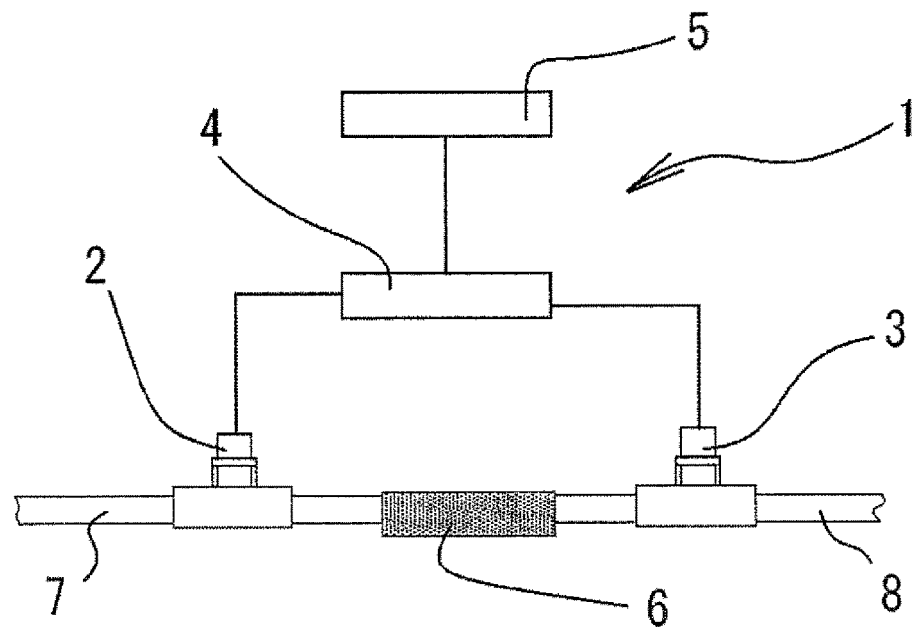
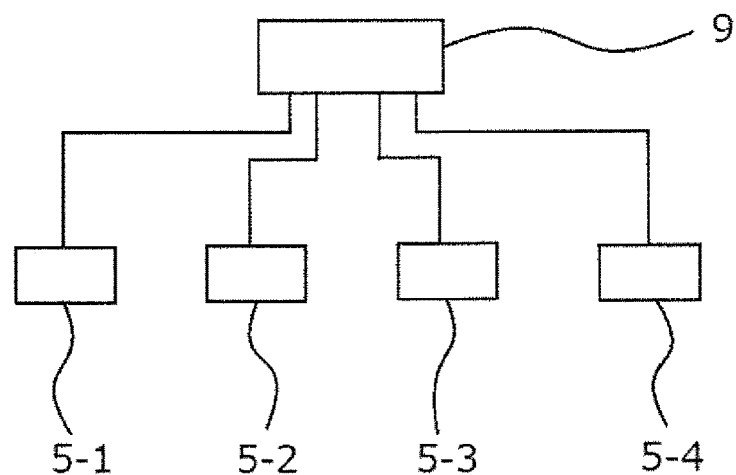
Figure 2

DETERMINATION DEVICE FOR DETERMINING AN IMPROVEMENT IN WATER QUALITY

TECHNICAL FIELD

The present invention relates to a determination device for determining an improvement in water quality. More particularly, the present invention relates to a determination device capable of determining, easily and in a short time, an enhancement in the quality of water treated with a water quality-improving device.

BACKGROUND ART

In general, when a metal piece is immersed in water for a long time, the surface of the metal piece becomes corroded. Metal corrosion is caused by localized polarization of parts of the surface into an anode and a cathode. A small amount of electric current flows between the anode and the cathode, which causes an oxidation reaction at the anode and a reduction reaction at the cathode. The oxidation reaction at the anode oxidizes the surface of the metal piece, whereby the metal corrosion progresses.

Various kinds of devices capable of improving the quality of water with ceramics that emits far-infrared rays have been conventionally known as water quality-improving devices. An example of the water quality-improving devices may be a device named "THE BIOWATER" (registered trademark), which is sold on market by TOSHIKOGYO CO., LTD. (see Non-patent document 1). It is reported that water treated with this device has various advantages. Especially noticeable is its effectiveness in preventing deterioration caused by red rust. More particularly, metal corrosion progresses more slowly in water having been treated with this water quality-improving device than in untreated water. In other words, the treatment of water with the water quality-improving device enhances antirust effect of water. When the water quality-improving device is installed, for example, in piping, through which the water that has been treated with the water quality-improving device is made to pass, the progress of metal corrosion on the inner surface of the piping is capable of being controlled.

It normally takes a time period from a few months to several years to assess the progress of metal corrosion by observing and analyzing the surface of metal pieces immersed in water. Conventionally, it also takes a time period from a few months to several years from the installation of a water quality-improving device in piping to determine the effectiveness of the device in controlling metal corrosion on the inner surface of the piping. Thus, currently it is not possible to determine an improvement in the rust-prevention of treated water within a short time period from the installation.

Also, in general, a water quality-improving device is usually placed in piping of large facilities such as factories and buildings. When an improvement in the quality of water that has been treated with a water quality-improving device is determined by examining the piping in which the water quality-improving device is installed, it is necessary to temporarily stop operation of the equipment provided with the device, to drain water from the piping, and then to observe the inner surface of the piping. However, it is often practically difficult to stop operation of the equipment and it requires heavy labor to drain water from the piping. Thus it is difficult to check whether the anti-corrosion performance of water is enhanced owing to the installation of a water quality-improving device by examining the piping in which the water quality-improving device is installed.

A determination device for determining an improvement in water quality capable of determining an enhancement in the quality of treated water within a short time period has been proposed (patent document 1). This determination device for determining an improvement in water quality has excellent performance; "it does not take a long time period from a few months to several years to observe the progress of corrosion in order to determine the effectiveness of the device in controlling metal corrosion, but just a short period of several days to check an enhancement in the antirust effect of water."

We will explain the technical significance of water quality improvement hereinafter, referring to the determination device for determining an improvement in water quality disclosed in patent document 1.

The inner walls of iron pipes for the distribution of city water, which contact city water, become rusty as a long time passes. Due to various factors, the inner walls of iron pipes have parts that easily rust, or anode parts, and parts that hardly rust, or cathode parts. The electric potential at the anode parts becomes different from the electric potential at the cathode parts. This electric potential difference causes corrosion current to flow between the anode parts and the cathode parts, which is a corrosion reaction. The corrosion current moves cations in city water to the cathode parts and anions therein to the anode parts. These movements of ions cause secondary reactions. The secondary reactions result in, for example, formation of calcium carbonate films on the surface of iron at the cathode parts, and formation of films containing red rust as a main component and silica substances on the surface thereof at the anode parts. The films formed at the cathode and anode parts check the movement of dissolved oxygen and various ions, which is necessary to the corrosion reaction. Thus the rate of corrosion on the inner walls of iron pipes is somewhat lowered. Although the corrosion rate is decreased, the corrosion reaction still continues and corrosion progresses because the films are not formed on the entire surface of the inner walls.

Researches by the inventors of the present invention revealed that the properties of the calcium carbonate films formed at the cathode parts by the corrosion reaction were changed by the treatment with a water quality-improving device, such as "THE BIOWATER".

The inventors of the present invention also found the following: The calcium carbonate in the calcium carbonate films formed from water whose quality has not been improved with a water quality-improving device has a crystal structure of aragonite. The aragonitic crystals are in the form of needles, and the films thereof are rough and have small electric resistance. On the other hand, the calcium carbonate in the calcium carbonate films formed from water whose quality has been improved with a water quality-improving device has a crystal structure of calcite. The calcitic crystals are in the form of granules, and the films thereof are densely formed and have large electric resistance.

Calcium carbonate films become densely formed on the inner surfaces of pipes that contact water whose quality has been improved by the water quality improvement with the water quality-improving device, because the change in the crystal structure of calcium carbonate prevents dissolved oxygen from being supplied to the cathode parts. As a result of the formation of dense calcium carbonate films, the movement of dissolved oxygen that are necessary to corrosion reactions is prevented and the electric resistance of the calcium carbonate films becomes larger. Thus, the corrosion rate of iron on the inner surfaces of iron pipes is decreased.

The decrease in the corrosion rate also delays the growth of films of red rust, or iron oxide, at the anode parts, and further densifies red rust films per se.

As a result, the oxygen supply to the surface of the iron at the parts with red rust is decreased, which changes the red rust to black rust. In other words, the life of Wüstite (FeO) is made longer, which enables Wüstite to react with red rust ($Fe_2O_3$) to form magnetite. As time lapses, a dense black rust layer is formed from the surface side of the iron inner walls, which keeps iron atoms from being ionized.

The invention disclosed in patent document 1 teaches placing first electrodes in water whose quality is not improved, such as city water, and second electrodes in water whose quality is improved; measuring an electric resistance between the first electrodes and the second electrodes; and determining an improvement in water quality. The determination device for determining an improvement in water quality disclosed in patent document 1 is capable of determining an enhancement in the antirust effect of water in just a short period of several days, which is excellent performance.

However, determination devices for determining an improvement in water quality that require a shorter time period to determine an enhancement in the antirust effect of water whose quality has been improved are desired.

Conductivity meters, or electroconductivity meters, are commercially available. On the websites of business corporations that manufacture and sell commercially available conductivity meters are carried technological stories like the following: The degree of filthiness of industrial wastewater or of water discharged from sewage treatment plants is determined based on electric conductivity measured with a conductivity meter; pH and electric conductivity are effective as indicators to show the degree of rainwater pollution, and the degree is monitored with a conductivity meter; an electric conductivity of a food is measured with a conductivity meter and the salinity of the food is calculated from the resulting electric conductivity; and the electric conductivity measured with a conductivity meter is employed as an indicator of the purity of water when ultrapure water is produced. Judging from the stories on such websites, conductivity meters have been used mainly as a measuring instrument to measure electric conductivity.

PRIOR ART DOCUMENTS

Non-Patent Documents

Non-patent Document 1: "Introduction of the Products" on the website of TOSHIKOGYO CO, LTD. whose URL is http://www.biowater.co.jp/product/feature.html (searched on Apr. 21, 2014).
Patent Document 1: WO 2015/181859

SUMMARY OF THE INVENTION

Problems to be Solved by the Invention

The objective of the present invention is to provide a determination device for determining an improvement in water quality, capable of determining, easily and in a short time, specifically in less than a few days, an enhancement in quality, such as rust prevention, of water treated with a water quality-improving device.

Means to Solve the Problems

Means to achieve the objective are as follows:
(1) A determination device for determining an improvement in water quality comprising a first measuring device for measuring by AC terminal electric conductimetry a capacitance of a first capacitor formed between a pair of first electrodes that are immersed in water to be supplied to a water quality-improving device; a second measuring device for measuring by AC terminal electric conductimetry a capacitance of a second capacitor formed between a pair of second electrodes that are immersed in water that has been treated with the water quality-improving device; and a processor for calculating a ratio (Y/X) of a capacitance Y to a capacitance X, wherein the capacitance X is a capacitance of the first capacitor in the water to be supplied to the water quality-improving device, outputted by the first measuring device when an AC frequency is not more than 100 Hz; and the capacitance Y is a capacitance of the second capacitor in the water that has been treated with the water quality-improving device, outputted by the second measuring device at the same AC frequency.
(2) The determination device according to item (1), wherein the AC frequency is from 0.1 to 100 Hz.
(3) The determination device according to item (1) or (2), wherein the processor comprises a corrector for correcting the ratio (Y/X) of the capacitance Y outputted by the second measuring device to the capacitance X outputted by the first measuring device based on a capacitance outputted by the first measuring device when a high frequency of not less than 10 kHz is applied between the pair of first electrodes and a capacitance outputted by the second measuring device when the high frequency is applied between the pair of second electrodes.
(4) The determination device according to any one of items (1)-(3), wherein the processor is installed at a place remote from a location where the water quality-improving device is installed, and measured data are sent from the first and second measuring devices to the processor through wire or by radio.
(5) The determination device according to any one of items (1)-(4), wherein the determination device comprises a judging device for judging that the water quality improvement has been carried out effectively when the ratio outputted by the processor exceeds a predetermined threshold.
(6) The determination device according to any one of items (1)-(5), wherein the determination device comprises an alarming device for raising an alarm when the ratio is not more than the threshold.
(7) The determination device according to item (6), wherein the judging device and the alarming device are installed at a place or places remote from a location where the water quality-improving device is installed, and the judging device, the alarming device, and the processor are connected with each other through wire or by radio.
(8) The determination device according to any one of items (1)-(7), wherein the water quality-improving device brings water into contact with a hybrid ceramic which emits far-infrared rays having wavelengths from 4.4 μm to 15.4 μm at an integral emissivity of 92% or more.

Advantages of the Invention

The determination device according to the present invention is capable of instantly determining an improvement in water quality based on the ratio (Y/X) of the second capacitance (Y) of the second capacitor, formed in water that has been treated with the water quality-improving device, to the first capacitance (X) of the first capacitor, formed in untreated water, the ratio calculated by the processor, wherein the second capacitance is measured by AC terminal electric conductimetry with the second measuring device, and the first capacitance is measured by AC terminal electric conductimetry with the first measuring device, wherein the alternating current has an AC frequency of not more than 100 Hz, preferably from not less than 1 Hz to not more than 100 Hz.

Contrary to the common technical knowledge that it is necessary to increase the frequency in order to precisely measure an electric conductivity by AC terminal electric conductimetry, such as AC two-terminal electric conductimetry, the device according to this invention is capable of easily determining how the quality of treated water is improved, compared with the quality of untreated water, by applying an alternating current with a low frequency of not more than 100 Hz, within a short period of time.

The determination device for determining an improvement in water quality according to the present invention has a processor with a corrector, which enables the determination device to accurately determine an improvement in water quality even if the cell constant of the first measuring device and that of the second measuring device are changed.

The present invention makes it possible to install the processor or the judging device, which deals with data outputted by the processor, at a place remote from the location where the first and second measuring devices are installed. When measured data outputted by the first and second measuring devices or calculated data outputted by the processor are arranged to be sent to the judging device through wire or by radio, data outputted by the first and second measuring devices installed at several locations, especially at a plurality of locations, may be centrally controlled from one place.

Thus, the present invention makes it possible to centrally control, from a control room, data measured by determination devices for determining an improvement in water quality placed everywhere in Japan or in various countries of the world, and to judge the degree of improvement in the quality of water by each water quality-improving device into which the determination device is incorporated.

The determination device for determining an improvement in water quality according to the present invention makes it possible to place the first and second measuring devices at many remote locations, to centrally control from one place data outputted by the first and second measuring devices, centrally analyzing the effects of water quality improvement affected by differences in areas and in water qualities, and to carry out appropriate maintenance of the water quality-improving devices.

BRIEF DESCRIPTION OF THE DRAWINGS

FIG. 1 is a schematic illustration showing a combination of a determination device for determining an improvement in water quality according to the present invention and a water quality-improving device.

FIG. 2 is a schematic illustration showing another example of a determination device for determining an improvement in water quality according to the present invention.

EMBODIMENTS TO CARRY OUT THE INVENTION

What is important to this invention is that the determination device determines an improvement in water quality not by respectively measuring the electric conductivity of water the quality of which has been improved and that of untreated water but by measuring the capacitance of a second capacitor formed in the improved water and that of a first capacitor formed in the untreated water.

In the following, we will explain the reason that an improvement in water quality is determined not by measuring the electric conductivity but by measuring the capacitance of the capacitor.

The treatment of city water with the water quality-improving device, for example a hybrid ceramic, provides the city water with various effective properties such as bacteriostatic capability, antioxidative capability, detergent ability, environmental cleanup capability, treated condition-sustaining capability, and anticorrosion property. In order to search for the cause of the effective properties, the inventors of the present invention studied the electric conductivity of a solution and the capacitance of a capacitor formed therein. As a result, it turned out that the water quality improvement caused a difference between the capacitance of a second capacitor formed in water whose quality had been improved and the capacitor of a first capacitor formed in water whose quality had not been improved when the applied alternating current had a low AC frequency. It also turned out that the water quality improvement caused no difference between the capacitance of a first capacitor formed in water before the water quality-improving treatment and the capacitance of a second capacitor formed in water after the treatment when the applied alternating current had an AC frequency of not less than a certain value.

An example of the determination device for determining an improvement in water quality according to the present invention is shown in FIG. 1. As shown in FIG. 1, the determination device for determining an improvement in water quality 1 has a first measuring device 2, a second measuring device 3, and a processor 4. In a preferable embodiment, it further has a judging device 5.

This determination device for determining an improvement in water quality 1 is a device for judging an improvement in water quality made by, for example, a water quality-improving device 6. The water quality-improving device 6 may include devices having a hybrid ceramic, such as "THE BIOWATER" (registered trademark) manufactured by TOSHIKOGYO CO., LTD., which hybrid ceramic is placed in piping. The hybrid ceramic is one which emits far-infrared rays having wavelengths from 4.4 μm to 15.4 μm at an integral emissivity of 92% or more. City water treated with this hybrid ceramic is improved in at least one of a bacteriostatic capability, an antioxidative capability, a detergent ability, an environmental cleanup capability, a treated condition-sustaining capability, and an anticorrosion property (see non-patent document 1).

With this water quality-improving device 6 is coupled a supply piping 7 for supplying water, for example city water, to the device 6 through an upstream inlet thereof and a discharge piping 8 for discharging quality-improved water from the device 6 through a downstream outlet thereof.

The first measuring device 2 is placed at an appropriate position in the supply piping 7. The first measuring device 2 has an arrangement capable of measuring the capacitance of a capacitor formed in water, for example city water, by AC terminal electric conductimetry, such as AC two-terminal electric conductimetry or AC four-terminal electric conductimetry. The first measuring device 2 with an arrangement for carrying out AC two-terminal electric conductimetry has a pair of electrodes to be immersed in water that will be measured. An alternating current with a predetermined frequency is applied to the pair of electrodes. The frequency of the alternating current applied to the pair of electrodes is changed by orders from outside devices, such as a control unit not shown in the figures. The AC frequency of the applied alternating current of the first measuring device 2 may be set to a given frequency between 1 Hz and 200 Hz. The frequency may also be switched to another frequency within the range.

A commercially available LCR meter may be employed for the first measuring device 2. Commercially available LCR meters are capable of measuring the capacitance of a capacitor formed between a pair of electrodes.

Detected data outputted by the first measuring device 2 are inputted into a processor.

The second measuring device 3 may employ the same arrangement as the first measuring device 2 has. Also, the second measuring device 3 may be a device of the same model as the first measuring device 2. Detected data outputted by the second measuring device 3 are inputted into the processor.

The processor 4 calculates a ratio (Y/X) of the second capacitance of the second capacitor to the first capacitance of the first capacitor, from data outputted by the first measuring device 2, which is the capacitance of the first capacitor formed between a pair of electrodes of the first measuring device 2, the first capacitance (X) of the first capacitor formed in untreated water, and from data outputted by the second measuring device 3, which is the capacitance of the second capacitor formed between a pair of electrodes of the second measuring device 3, the second capacitance (Y) of the second capacitor formed in treated water.

The judging device 5 compares the ratio (Y/X) outputted by the processor 4 with a predetermined threshold. When the ratio exceeds the predetermined threshold, the judging device recognizes that the water quality-improving device 6 has improved water quality. On the other hand, when the ratio is not more than the threshold, the judging device denies an improvement of the water quality by the water quality-improving device 6.

The predetermined threshold is usually a given value more than one (1). Under some circumstances, however, the threshold may be set to an appropriate value more than one (1), such as 1.1, 1.2, or 1.3. What is meant by that the ratio of the second capacitance to the first capacitance is essentially one (1) is that water which has been supplied to the water quality-improving device and treated thereby is not improved in its quality. That the ratio of the second capacitance to the first capacitance is essentially one (1) means that it is not problematical if one considers the value outputted by the first measuring device to be the same as the value outputted by the second measuring device, although the ratio (Y/X) calculated from the outputted data is not exactly the integer one (1); data outputted by the first and second measuring devices may have errors caused by differences in measuring devices and electrodes, which errors should be taken into account.

This processor may have a corrector.

When the pair of electrodes of the first measuring device 2 is immersed in water in the supply piping 7 of the water quality-improving device 6 for a long time, and the pair of electrodes of the second measuring device 3 is immersed in water in the discharge piping 8 thereof for a long time, the surface of the electrodes becomes dirty, which causes changes in data outputted by the first measuring device 2 and the second measuring device 3. As understood, the reason why data outputted by the first measuring device 2 and the second measuring device 3 vary as time passes is that the dirt causes changes of the cell constants with the passage of time.

The ratio (Y/X) of the second capacitance to the first capacitance, which changes as a result of changes of the cell constants with the passage of time, may be corrected in the following way.

The correction of the ratio (Y/X) of the second capacitance to the first capacitance should preferably be carried out each time the first capacitance of the first capacitor formed in water to be supplied to the water quality-improving device is measured by the first measuring device 2 and the second capacitance of the second capacitor formed in water discharged from the water quality-improving device is measured by the second measuring device 3. Under certain circumstances, the correction may be carried out at longer intervals, every three measurements or every five measurements.

The correction of the ratio (Y/X) of the second capacitance of the second capacitor to the first capacitance of the first capacitor may be carried out by applying an alternating current with a high frequency of not less than 10 kHz to the electrodes of the first measuring device 2 and to those of the second measuring device 3. During the researches on water improvement with the water quality-improving device by the inventors of the present invention, they observed that the ratio (Y/X) of the second capacitance (Y) of the second capacitor outputted by the second measuring device 3 when the alternating current applied to the electrodes of the second measuring device 3 that were immersed in water discharged from the water quality-improving device, or in water which had been supplied to the water quality-improving device and the quality of which had been improved, had a frequency of not less than 10 kHz, to the first capacitance (X) of the first capacitor outputted by the first measuring device 2 when the alternating current applied to the electrodes of the first measuring device 2 that were immersed in water to be supplied to the water quality-improving device had a frequency of not less than 10 kHz, became essentially one (1). Based on these observations, when the cell constant of the first measuring device 2 and that of the second measuring device 3 vary for some reasons, the value of the ratio (Y/X) of the second capacitance of the second capacitor to the first capacitance of the first capacitor, which are calculated from data outputted by the first measuring device 2 and the second measuring device 3, should be corrected so that the ratio (Y/X) will be one (1).

Specifically, when each of the alternating currents to be applied respectively to the electrodes of the first measuring device 2 and those of the second measuring device 3 has a low frequency, such as 100 Hz, let the measured value outputted by the first measuring device 2 be denoted by $X_{100}$ and the measured value outputted by the second measuring device 3 by $Y_{100}$. Then, when an alternating current that is applied to the electrodes of the first measuring device 2 has a high frequency of not less than 10 kHz, for example a given frequency between 10 kHz and 100 kHz, let the measured value outputted by the first measuring device 2 be denoted by $X_{10}$. Let the measured value outputted by the second measuring device 3 be denoted by $Y_{10}$ when an alternating current having the same high frequency as the alternating current applied to the electrodes of the first measuring device 2 has is applied to the second measuring device 3.

The correction is calculated in the following way.

For water to be supplied to the water quality-improving device: $C1 = X_{100}/X_{10}$ For water discharged from the water quality-improving device: $C2=Y_{100}/Y_{10}$ When the resulting value of the division C1/C2 exceeds one (1), an improvement in water quality is recognized. On the other hand, when the resulting value is essentially one (1), improvements in water quality are denied.

The corrector has a calculating function to carry out the correction and corrects the values calculated by the processor. Thus the judging device 5 is capable of judging the ratio (Y/X) of the second capacitance of the second capacitor to the first capacitance of the first capacitor correctly, when the sensitivity of the electrodes of the first measuring device 2 and that of the electrodes of the second measuring device 3 vary as time passes.

The first measuring device 2 and second measuring device 3 of the determination device for determining an improvement in water quality according to the present invention may be installed in a place where it is necessary to judge whether the water quality is improved. On the other hand, the judging device 5 may be installed not only at a place where the judgment of an improvement in water quality is required but also at a place remote from the first measuring device 2 and the second measuring device 3. Furthermore, both of the processor 4 and the judging device 5 may be installed at a place remote from the first measuring device 2 and the second measuring device 3. Data outputted by the processor 4 may be transmitted to the judging device 5 through wire or by radio. Data outputted by the first measuring device 2 and second measuring device 3 may also be transmitted to the processor 4 through wire or by radio.

As shown in FIG. 2, the determination device for determining an improvement in water quality may be designed in the following way: A pair of first and second measuring devices 2, 3 is installed in each of the places, areas or facilities where it is necessary to check whether or not water quality is improved. A central controlling and monitoring device 9 placed in a single central controlling and monitoring room may be designed to monitor several pairs of data wherein each pair of data is outputted by each pair of the first measuring device 2 and the second measuring device 3.

The central controlling and monitoring device 9 is capable of checking whether water quality is improved by the water quality-controlling devices 6 that are installed in various areas and places, based on the data outputted by the pairs of first and second measuring devices 2, 3 installed in the corresponding areas and places. The central controlling and monitoring device 9 is capable of controlling the AC frequency of the alternating current to be applied to the electrodes of the first measuring device 2 and those of the second measuring device 3.

The central controlling and monitoring device 9 may be composed of various elements including a display, such as a liquid crystal display or a big screen, a computer for controlling various devices, and a controller for controlling the AC frequency of the alternating current to be applied to the electrodes of the first measuring device 2 and those of the second measuring device 3.

Into the central controlling and monitoring room, where the central controlling and monitoring device 9 is installed, are also integrated the processors 4 each of which receives detection data outputted by the first measuring device 2 and the second measuring device 3, which are coupled with the water quality-improving device 6 installed in each of the places where water quality improvement is desired; the judging device(s) 5 for judging an improvement in water quality based on the ratios (Y/X) calculated by the processors 4; and alarm devices that may be installed if necessary.

The alarm device is a device which raises an alarm, specifically sounds alarms and/or turns on warning lights, or shows warning indicators on the display, especially when the ratio (Y/X) of the second capacitance of the second capacitor to the first capacitance of the first capacitor is not more than 1.

This central controlling and monitoring device 9 enables monitoring personnel in a single central controlling and monitoring room to judge whether proper water quality improvement is carried out by the water quality-improving device 6 even when the water quality-improving device 6 is installed in a remote place, area, or facility where water quality improvement is required. Also, the central controlling and monitoring device is capable of changing the AC frequency of the alternating current to be applied by the first measuring device 2 and second measuring device 3 which are installed at a remote place.

In the previous examples, the first measuring device 2 is installed in the supply piping 7 coupled with the water quality-improving device 6 that is placed in the piping through which water flows, and the second measuring device 3 in the discharge piping 8 coupled with the water quality-improving device. The first measuring device 2 may be placed in a vessel for sampled water, such as a beaker or a bucket, which is connected with a pipe branching off from the supply piping 7. In the same way, the second measuring device may be placed in a vessel for sampled water, such as a beaker or a bucket, which is connected with a pipe branching off from the discharge piping 8.

EXAMPLES

We will show examples where water quality improvement was actually judged by means of the determination device for determining an improvement in water quality in the following.

As shown in FIG. 1, "THE BIOWATER (registered trademark)" manufactured by TOSHIKOGYO CO., LTD., as a water quality-improving device, was placed in a piping through which water flew. A LCR meter, a model ZM2372 component measuring equipment manufactured by NF Corporation, as a first measuring device 2, was installed in a supply piping 7 coupled with the water quality-improving device. A LCR meter of the same model, as a second measuring device 3, was installed in a discharge piping 8. The sensor of the LCR meters was a model 9382-10 waterproof submersible-type conductivity cell manufactured by HORIBA, Ltd.

City water was allowed to flow through the supply piping 7, the water quality-improving device 6, and the discharge piping 8, for the first experiment.

The supply of city water was begun and the AC frequency of the applying alternating current of the LCR meters was set to the values shown in Table 1. After a predetermined period of time passed, a first capacitance of the first capacitor outputted by the LCR meter for the alternating current of each AC frequency, which served as a first measuring device 2, was recorded and a second capacitance of the second capacitor outputted by the LCR meter for the alternating current of each AC frequency, which served as a second measuring device 3, was recorded. The outputted data are shown in Table 1.

The ratio (Y/X) of the second capacitance of the second capacitor to the first capacitance of the first capacitor for the alternating current of each AC frequency is shown in Table 1.

TABLE 1

| Applied AC frequency | Water (untreated) Capacitance of the capacitor measured with the first LCR meter (X) (nF) | Water (treated) Capacitance of the capacitor measured with the second LCR meter (Y) (nF) | (Y)/(X) |
|---|---|---|---|
| 1 Hz | 930 | 1005 | 1.081 |
| 10 Hz | 34.4 | 38.3 | 1.113 |
| 20 Hz | 13.8 | 15.4 | 1.116 |
| 50 Hz | 4.17 | 4.66 | 1.118 |
| 100 Hz | 1.76 | 1.95 | 1.108 |
| 200 Hz | 0.80 | 0.87 | 1.088 |
| 1 KHz | 0.208 | 0.212 | 1.019 |
| 10 KHz | 0.145 | 0.145 | 1.000 |
| 20 KHz | 0.144 | 0.144 | 1.000 |
| 100 KHz | 0.142 | 0.142 | 1.000 |

In order to ensure reproducibility, the same experiment as the first experiment was carried out as a second experiment, when one week passed after the completion of the first experiment.

The results of the second experiment are shown in Table 2.

TABLE 2

| Applied AC frequency | Water (untreated) Capacitance of the capacitor measured with the first LCR meter (X) (nF) | Water (treated) Capacitance of the capacitor measured with the second LCR meter (Y) (nF) | (Y)/(X) |
|---|---|---|---|
| 1 Hz | 1052 | 1144 | 1.087 |
| 10 Hz | 39.3 | 44.1 | 1.122 |
| 20 Hz | 15.7 | 17.7 | 1.127 |
| 50 Hz | 4.90 | 5.54 | 1.131 |
| 100 Hz | 1.96 | 2.21 | 1.128 |
| 200 Hz | 0.87 | 0.97 | 1.115 |
| 1 KHz | 0.218 | 0.223 | 1.023 |
| 10 KHz | 0.146 | 0.146 | 1.000 |
| 20 KHz | 0.145 | 0.144 | 1.000 |
| 100 KHz | 0.144 | 0.142 | 1.000 |

The results shown in Tables 1 and 2 show that the ratio of the second capacitance of the second capacitor to the first capacitance of the first capacitor at each of the low AC frequencies from 1 Hz to 200 Hz exceeds one (1). Thus it can be determined that the water quality-improving device changed the quality of water. In addition, the reproducibility of the improvement is excellent.

The employment of these LCR meters made it possible to instantly determine an improvement in water quality by the water quality-improving device.

EXPLANATION OF REFERENCE SIGNS 1 determination device for determining an improvement in water quality

We claim:

1. A determination device for determining an improvement in water quality comprising:
   a first LCR meter for measuring a capacitance of a first capacitor formed between a pair of first electrodes that are immersed in water to be supplied to a water quality-improving device, while applying an AC voltage with a predetermined AC frequency to the pair of first electrodes;
   a second LCR meter for measuring a capacitance of a second capacitor formed between a pair of second electrodes that are immersed in water that has been treated with the water quality-improving device, while applying an AC voltage with the predetermined AC frequency to the pair of second electrodes; and
   a processor for calculating a ratio (Y/X) of a capacitance Y to a capacitance X, wherein the capacitance X is a capacitance of the first capacitor between the pair of first electrodes immersed in the water to be supplied to the water quality-improving device as outputted by the first LCR meter when the predetermined AC frequency is not more than 100 Hz; and the capacitance Y is a capacitance of the second capacitor between the pair of second electrodes immersed in the water that has been treated with the water quality-improving device as outputted by the second LCR meter at the predetermined AC frequency;
   wherein the calculated ratio is indicative of an improvement in a rust-prevention quality in the water treated with the water quality-improving device.

2. The determination device according to claim 1, wherein the predetermined AC frequency is from 0.1 to 100 Hz.

3. The determination device according to claim 1, wherein the processor comprises a corrector for correcting the ratio (Y/X) of the capacitance Y outputted by the second LCR meter to the capacitance X outputted by the first LCR meter based on a capacitance outputted by the first LCR meter when a high frequency of not less than 10 kHz is applied between the pair of first electrodes and a capacitance outputted by the second LCR meter when the high frequency is applied between the pair of second electrodes.

4. The determination device according to claim 3, wherein the corrector corrects the capacitance X outputted by the first LCR meter to C1=X100/X10, and the corrector corrects the capacitance Y outputted by the second LCR meter to C2=Y100/Y10, where
   X100 is a measured value outputted by the first LCR meter when alternating currents with a frequency of between 0.1 to 100 Hz is applied to the electrodes of the first LCR meter,
   X10 is a measured value outputted by the first LCR meter when alternating currents with a frequency between 10 kHz and 100 kHz is applied to the electrodes of the first LCR meter,
   Y100 is a measured value outputted by the second LCR meter when alternating currents with a frequency of between 0.1 to 100 Hz is applied to the electrodes of the second LCR meter, and
   Y10 is a measured value outputted by the second LCR meter when alternating currents with a frequency of between 10 kHz and 100 kHz is applied to the electrodes of the second LCR meter.

5. The determination device according to claim 1, wherein the processor is installed at a place remote from a location where the water quality-improving device is installed, and measured data are sent from the first and second LCR meters to the processor through wire or by radio.

6. The determination device according to claim 1, wherein the determination device comprises a judging device for judging that the water quality improvement has been carried out effectively when the ratio outputted by the processor exceeds a predetermined threshold.

7. The determination device according to claim 6, wherein the determination device comprises an alarming device for raising an alarm when the ratio is not more than the threshold.

8. The determination device according to claim 7, wherein the judging device and the alarming device are installed at a place or places remote from a location where the water quality-improving device is installed, and the judging device, the alarming device, and the processor are connected with each other through wire or by radio.

9. The determination device according to claim 1, wherein the water quality-improving device brings water into contact with a hybrid ceramic which emits far-infrared rays having wavelengths from 4.4 μm to 15.4 μm at an integral emissivity of 92% or more.

\* \* \* \* \*